(12) United States Patent
Mamigonians et al.

(10) Patent No.: US 11,484,244 B2
(45) Date of Patent: Nov. 1, 2022

(54) DETECTING IRREGULARITIES IN BREAST TISSUE

(71) Applicant: Zedsen Limited, London (GB)

(72) Inventors: Hrand Mami Mamigonians, London (GB); Aslam Sulaimalebbe, Cardiff (GB)

(73) Assignee: Zedsen Limited, London (GB)

( * ) Notice: Subject to any disclaimer, the term of this patent is extended or adjusted under 35 U.S.C. 154(b) by 922 days.

(21) Appl. No.: 16/229,318

(22) Filed: Dec. 21, 2018

(65) Prior Publication Data

US 2019/0328311 A1 Oct. 31, 2019

(30) Foreign Application Priority Data

Apr. 30, 2018 (GB) ..................................... 1807090

(51) Int. Cl.
*A61B 5/00* (2006.01)
*A61B 5/05* (2021.01)
*A61B 5/053* (2021.01)

(52) U.S. Cl.
CPC ............ *A61B 5/4312* (2013.01); *A61B 5/053* (2013.01); *A61B 5/6804* (2013.01); *A61B 2562/0209* (2013.01); *A61B 2562/046* (2013.01)

(58) Field of Classification Search
CPC ..... A61B 5/4312; A61B 5/053; A61B 5/6804; A61B 2562/0209; A61B 2562/046
See application file for complete search history.

(56) References Cited

U.S. PATENT DOCUMENTS

2004/0073131 A1* 4/2004 Organ ................. A61B 5/0536
600/547
2008/0076998 A1 3/2008 Organ et al.
(Continued)

FOREIGN PATENT DOCUMENTS

CN 203647341 U 6/2014
CN 105249549 A 1/2016
(Continued)

OTHER PUBLICATIONS

Corresponding International Patent Application No. PCT/GB2019/000008, International Search Report dated Apr. 17, 2019.
(Continued)

*Primary Examiner* — Eun Hwa Kim
*Assistant Examiner* — Adam Z Minchella
(74) *Attorney, Agent, or Firm* — Cooper Legal Group LLC

(57) ABSTRACT

A flexible dome-shaped substrate (301) defines an internal surface (403) arranged to accommodate breast tissue. A set of substantially circular electrodes (411, 412) are located concentrically on the substrate, along with a set of substantially radial electrodes (501, 502). An energizing circuit energizes a selected transmitter electrode to propagate an electric field through a detection region of the breast tissue during a coupling operation. A monitoring circuit receives an output signal from a selected receiver electrode. Positions are identified within the detection region by coordinates established by the substantially circular electrodes and the substantially radial electrodes. This allows irregularities to be identified and located.

19 Claims, 16 Drawing Sheets

(56) References Cited

U.S. PATENT DOCUMENTS

2009/0076336 A1\* 3/2009 Mazar .................... A61B 5/318
                                                                  600/300
2009/0216148 A1   8/2009 Freed et al.
2016/0296135 A1\* 10/2016 Yoo ...................... A61B 5/0022

FOREIGN PATENT DOCUMENTS

| CN | 105361866 A | 3/2016 |
| KR | 20110073002 A | 6/2011 |
| WO | 2003084381 A2 | 10/2003 |
| WO | 2013027120 A2 | 2/2013 |

OTHER PUBLICATIONS

Corresponding Great Britain Search Report, Application No. 1807090.4 dated Oct. 28, 2018, 1 page.

\* cited by examiner

DETECTING IRREGULARITIES IN BREAST TISSUE

CROSS REFERENCE TO RELATED APPLICATIONS

This application claims priority from United Kingdom Patent Application number 1807090.4, filed on Apr. 30, 2018, the whole contents of which are incorporated herein by reference.

BACKGROUND OF THE INVENTION

The present invention relates to an apparatus for identifying irregularities in breast tissue.

The present invention also relates to a method of detecting irregularities in breast tissue.

Techniques are known for detecting irregularities in breast tissue, primarily as a screening process for breast cancer. X-ray techniques are known but these present three significant problems. Firstly, expert operatives are required to manipulate sophisticated equipment, therefore specific appointments must be made for an individual to visit a facility at a specified time. Secondly, known techniques often involve the deployment of X-rays using solid metal contact plates resulting in an unpleasant experience if satisfactory images are to be obtained. Thirdly, the deployment of ionising radiation in itself presents health risks, therefore great care must be taken in terms of limiting the total exposure to radiation of this type.

It is also known to conduct physical examinations to identify physical irregularities such as lumps etc. However, a problem with this approach is that this may in turn result in a late intervention, whereas an earlier intervention would have been beneficial had the irregularity been detected sooner.

Experiments have shown that irregularities in breast tissue may be detected using electric fields, given that the permittivity and conductively of the breast tissue may change when an irregularity is present. However, difficulties arise in terms of deploying known equipment of this type, due to the inherent biology of actual living examples.

BRIEF SUMMARY OF THE INVENTION

According to a first aspect of the present invention, there is provided an apparatus for examining breast tissue, comprising: a flexible dome-shaped substrate defining an internal surface arranged to accommodate breast tissue; a set of substantially circular electrodes located concentrically on said substrate; a set of substantially radial electrodes located on said substrate; an energizing circuit for energizing a transmitter electrode selected from said plurality of electrodes to propagate an electric field through a detection region of said breast tissue during a coupling operation; and a monitoring circuit for receiving an output signal from a receiver electrode selected from the remaining electrodes of said plurality of electrodes, wherein positions are identified within said detection region by coordinates established by said substantially circular electrodes and said substantially radial electrodes.

In an embodiment, the apparatus further comprises multiplexing means configured to: select any available electrode for energizing as a transmitter electrode; and select a remaining electrode as a receiver electrode, wherein said transmitter electrode and said receiver electrode are capacitively coupled during a coupling operation. The multiplexing means may select a first set of electrodes for selectively energizing and monitoring; and said multiplexing means may then select the alternative second set of electrodes for selectively energizing and monitoring.

In an embodiment, spacings between adjacent substantially circular electrodes are of a substantially similar size.

In an embodiment, each radial electrode includes: first branches extending from a first side; and second branches extending from a second side. Each branch may define a first tip and a second tip; and distances between adjacent tips of adjacent branches may be substantially similar.

According to a second aspect of the present invention, there is provided a method of examining breast tissue using electric fields created by electrodes, wherein: a set of substantially circular electrodes are located concentrically on a flexible dome-shaped substrate; and a set of substantially radial electrodes are located on said flexible dome-shaped substrate, comprising the steps of:

energizing a selected transmitter electrode; monitoring a selected receiver electrode, to propagate electric fields through a detection region of said breast tissue during respective coupling operations; and identifying positions within said detection region by coordinates established by said substantially circular electrodes and said substantially radial electrodes.

Embodiments of the invention will be described, by way of example only, with reference to the accompanying drawings. The detailed embodiments show the best mode known to the inventor and provide support for the invention as claimed. However, they are only exemplary and should not be used to interpret or limit the scope of the claims. Their purpose is to provide a teaching to those skilled in the art.

Components and processes distinguished by ordinal phrases such as "first" and "second" do not necessarily define an order or ranking of any sort.

DETAILED DESCRIPTION OF EMBODIMENTS OF THE INVENTION

FIG. 1

Figure 1:
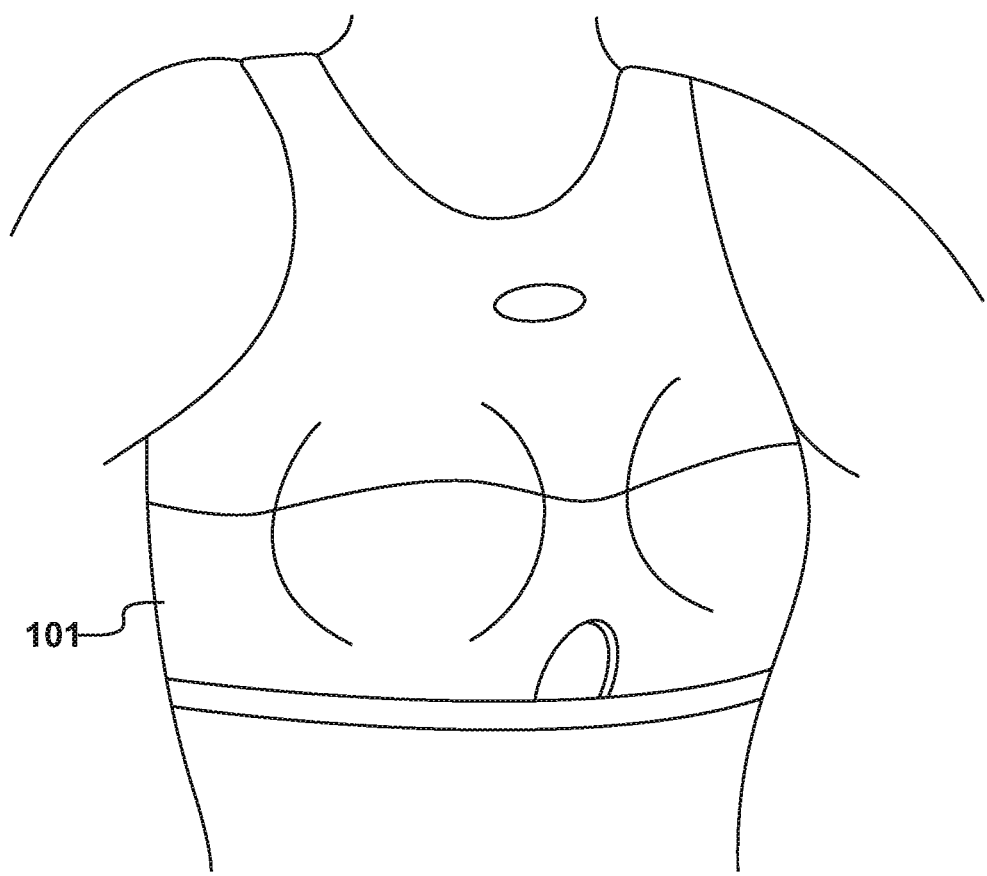
FIG. 1 shows a wearable item supporting apparatus embodying an aspect of the present invention.

A wearable item 101 is illustrated in FIG. 1 such that, supported within, there is an apparatus for identifying irregularities in breast tissue. Electrodes are mounted on a flexible substrate and the apparatus includes a control unit, which in turn houses an energizing circuit for energizing a selected transmitter electrode to generate an electric field, along with a monitoring circuit for receiving output signals from a selected receiver electrode. The flexible substrate is substantially dome-shaped and defines an internal surface arranged to accommodate breast tissue. In an embodiment, the apparatus may be deployed over a first breast and then over a second breast. However, in the embodiment of FIG. 1, a first flexible substrate is supported within the wearable item 101, along with a second flexible substrate that is also supported within the wearable item.

The embodiment of FIG. 1 is designed to be deployed by a user themselves and is configured to generate an alert signal if irregularities are detected. A user is therefore in a position to conduct an examination on a regular basis and seek further advice should any irregularities be detected. The device itself deploys relatively low-power electric fields, such that the deployment of these fields does not create any undesirable side-effects. In the embodiment of FIG. 1, the substantially dome-shaped apparatus is deployed such that an internal surface of the apparatus is in contact with a detection region. The substrates themselves are flexible and possibly constructed from a fabric material. A thin insulating layer is provided over the electrodes to electrically insulate them from contacting tissue, while minimizing the attenuation of penetrating electric fields.

FIG. 2

Figure 2:
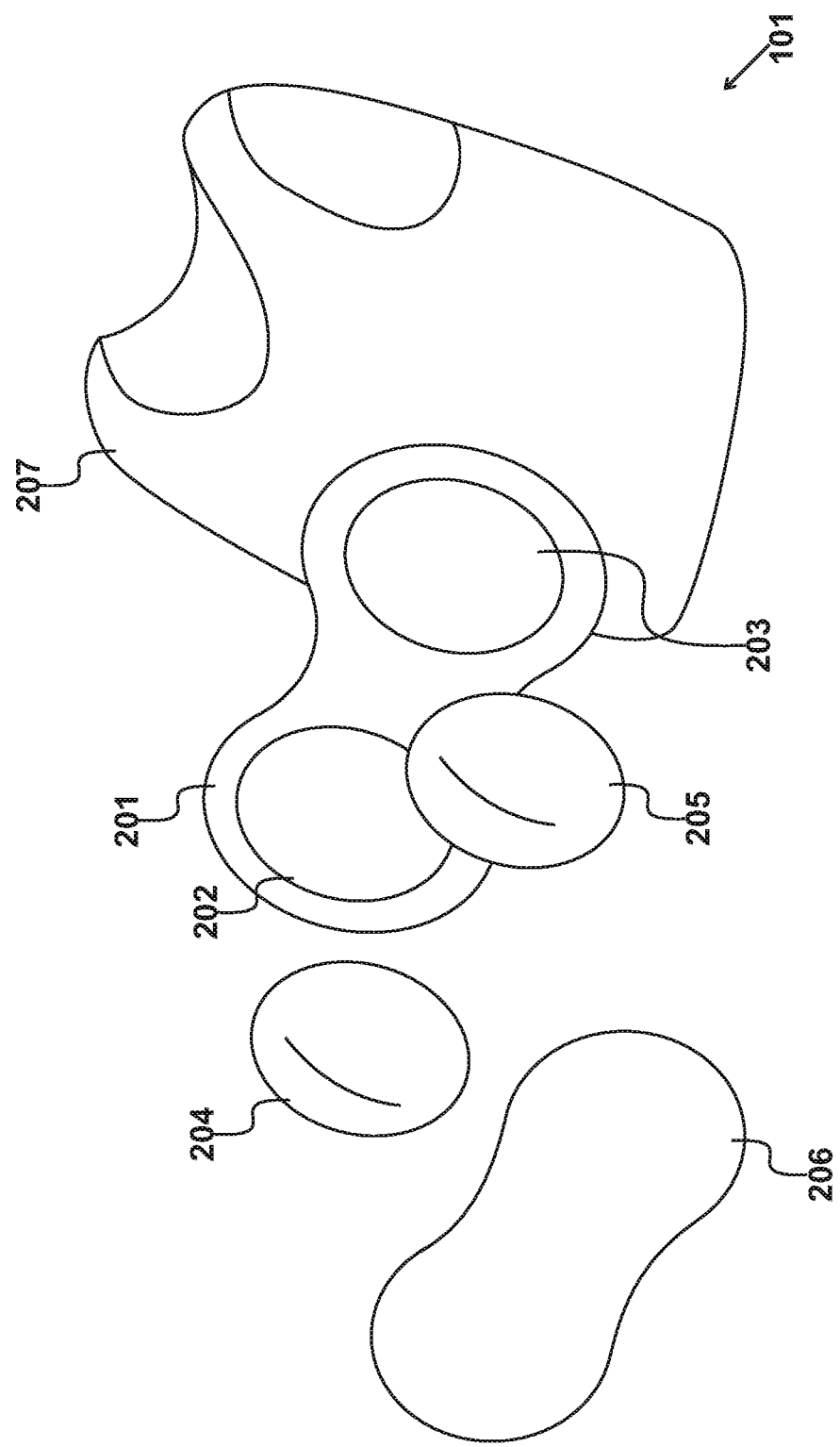
FIG. 2 shows an exploded view of the wearable item identified in FIG. 1.

An exploded view of the wearable item 101 is shown in FIG. 2, illustrating how the wearable item 101 may be assembled, to support the apparatus embodying an aspect of the present invention. The apparatus is supported on a frame 201, defining a first opening 202 and a second opening 203 configured to receive a right dome-shaped substrate 204 and a left dome-shaped substrate 205 respectively. The right dome-shape substrate and the left dome-shaped substrate are then covered by an outer cover 206, which is then attached to a main support vest 207.

FIG. 3

Figure 3:
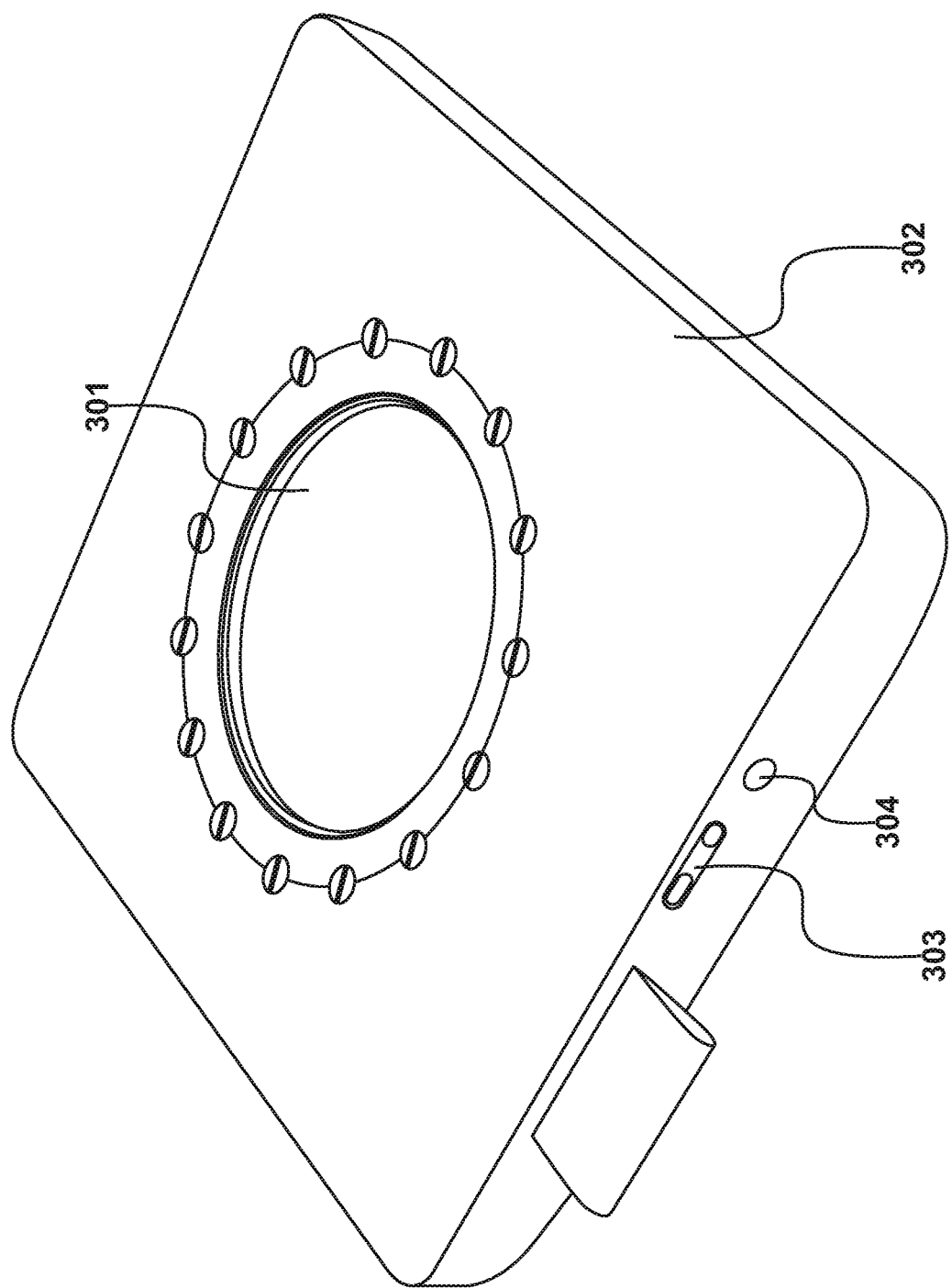
FIG. 3 shows an alternative apparatus embodying an aspect of the present invention.

An alternative configuration is shown in FIG. 3, in a form suitable for application in clinical environments by trained operatives. Again, electrodes are located on a flexible substrate 301 and an energising circuit, for energising a selected transmitter electrode to generate an electric field, is retained within a support housing 302. The support housing 302 also includes a scanning circuit for producing an output signal from a selected receiver electrode. Again, the flexible substrate 301 is substantially dome-shaped to define an internal surface arranged to accommodate breast tissue and, as described in detail with reference to subsequent figures, the electrodes are evenly arranged over the dome-shaped flexible substrate.

The device shown in FIG. 3 includes an activation switch 303 and a data-output port 304. In use, it is necessary for an operative to deploy the device over a first breast in order to perform a first identifying procedure. Thereafter, after collecting data, a similar procedure is deployed with respect to the second breast.

FIG. 4

Figure 4:
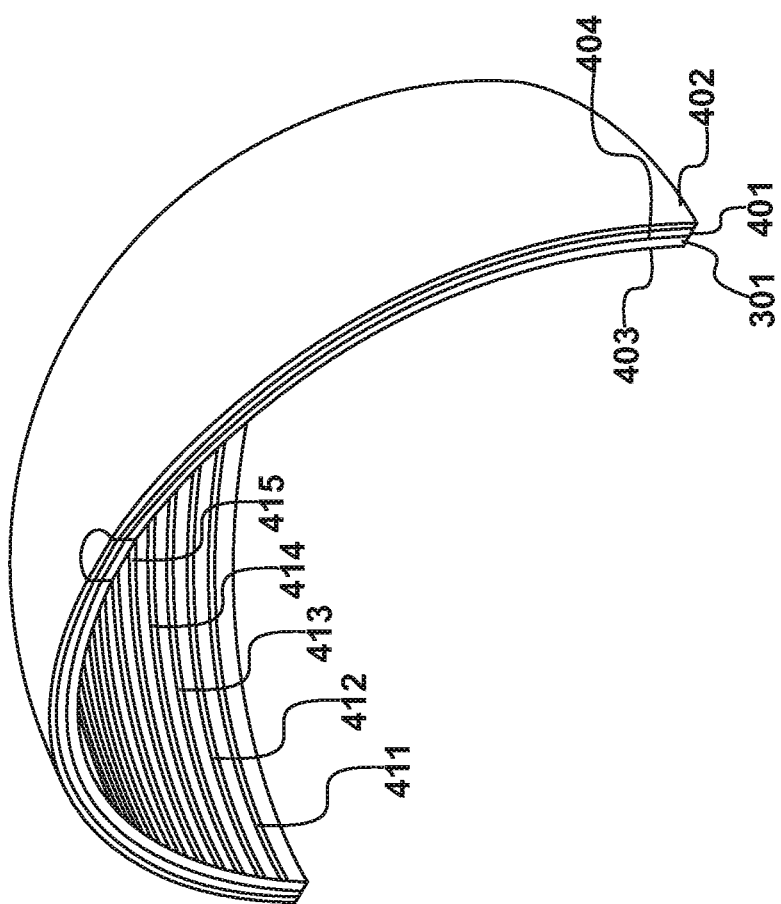
FIG. 4 shows an apparatus for identifying irregularities.

A cross-section of the flexible substrate 301 is shown in FIG. 4. The flexible substrate 301 is constructed from an insulating dielectric material. The flexible substrate 301 may be constructed from a knitted or woven fabric, thereby allowing the shape of the substrate 301 to adapt to the contours of the underlying biology. In this way, the apparatus remains comfortable, while ensuring that the capacitively coupled electrodes maintain an optimized relationship with respect to the tissue for which an attempt is being made to identify irregularities.

In the embodiment of FIG. 4, the flexible substrate 301 is supported by a silicone shell 401, which is in turn surrounded by a grounding cover 402. The grounding cover 402 is connected to ground and provides shielding to prevent external electric fields from inducing noise.

Electrodes, of which there are a plurality, are located on the flexible substrate, such that an energizing circuit may energize a selected transmitter electrode to generate an electric field and a monitoring circuit may in turn receive and sample output signals to provide output data. This output data may be retained locally or supplied to other external equipment, possibly via the data-output port 304.

In known scanning devices of this type, electrodes are traditionally mounted on a relatively rigid substrate and are arranged in a substantially Cartesian configuration; thereby ensuring the uniform generation of electric fields within the Cartesian geometry. It has been appreciated that it could be possible to deploy detectors of this type in order to propagate electric fields into breast tissue. Research has shown that irregularities in breast tissue often exhibit a change to their measurable electrical permittivity. However, the nature of the underlying geometry creates difficulties, in that the resulting electric fields are not uniform and create conditions that are difficult, if not impossible, to repeat. Consequently, it is likely that erroneous results would be obtained when comparing a first scan to a subsequent scan taken after a period of time. Given that the identification of irregularities often takes place with respect to comparisons taken over a period of time, such a situation renders the deployment of the known technology unsatisfactory.

To overcome these difficulties, it has been recognized that it is necessary for the substrate to accommodate the breast tissue, to ensure that close contact is made between the energized electrodes and the tissue upon which irregularities are being identified. The tissue is electrically insulated from the electrodes, achieved by a thin layer of an insulating material, but materials of this type should not attenuate the generated electric fields. Thus, as a first step, it has been appreciated that the substrate should a flexible substrate.

Furthermore, given the underlying geometry, to achieve close contact, the flexible substrate should be substantially dome-shaped to define an internal surface arranged to accommodate the breast tissue. Thus, it should be understood that as used herein, the term dome-shaped relates to an appropriate concaved shape that provides close accommodation to typical breast tissue and would not, when deployed, necessarily present a symmetrical geometric dome. However, it has also been appreciated that a geometry of this type provides significant advantages over planar structures and when being modelled mathematically, a more regular dome-shape may be considered as an approximation to the biology under consideration.

In addition, it has been appreciated that the use of a flexible material when deployed in a dome-shaped configuration does still not go far enough in terms of achieving the results required. Following known techniques, it would be possible to deploy substantially orthogonal Cartesian electrodes upon a flexible substrate that is substantially dome-shaped. However, again, such a deployment would result in an uneven distribution of electric fields, which in turn would create difficulties in terms of replicating the deployment. Consequently, in addition to providing a flexible substrate and in addition to providing a substantially dome-shaped substrate, the inventors have appreciated that the effectiveness of the apparatus is significantly enhanced (to an extent that a practical realization is achievable) by ensuring that the electrodes are evenly arranged over the dome-shaped flexible substrate. To achieve this, it has been appreciated that the underlying geometry should be respected, such that a radical modification is required in order to take the deployment of the electrodes away from the restrictive Cartesian configuration of known devices.

In the embodiment of FIG. 4, an even arrangement of electrodes has been achieved by providing circular electrodes that are arranged as concentric rings. In the embodiment of FIG. 4, the circular electrodes are located on an inner surface 403 of the flexible substrate 301. These are identified as a first set of electrodes and include a first circular electrode 411, a second circular electrode 412, a third circular electrode 413, a fourth circular electrode 414 and a fifth circular electrode 415. In an alternative embodiment, the first set of electrodes could be located on an outer surface 404 of the flexible substrate 301.

FIG. 5

In accordance with an aspect of the present invention, radial electrodes are included in addition to the circular electrodes, thereby providing two coordinates. An embodiment therefore includes a first set of circular electrodes and a second set of radial electrodes. One set is provided on the internal surface 403 and the other set is provided on the external surface 404.

Figure 5:
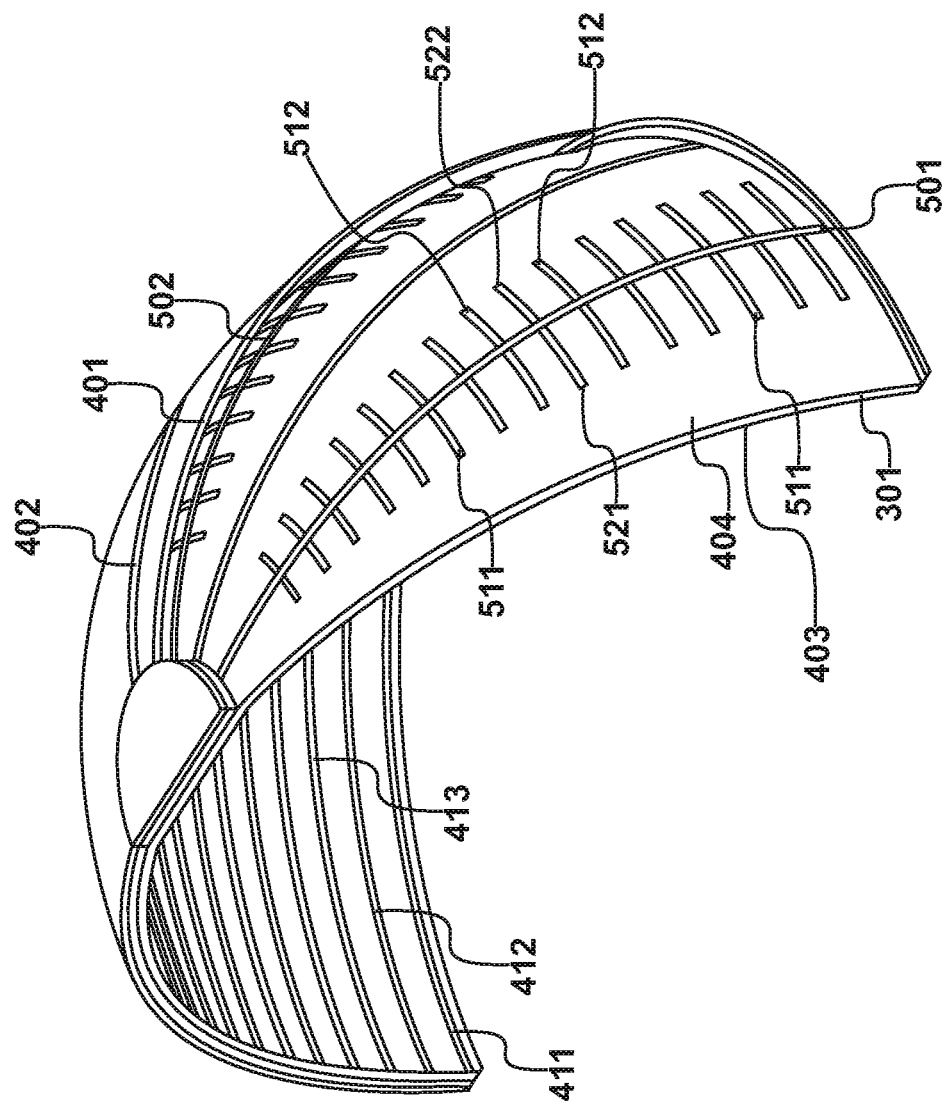
FIG. 5 shows a sectional view of the apparatus shown in FIG. 4.

In the embodiment of FIG. 5, radial electrodes have been positioned on the outer surface 404 of the dome-shaped flexible substrate 301. In FIG. 5, a portion of the grounding cover 402 and a portion of the silicone shell 401 have been removed, to reveal a first radial electrode 501 and a second radial electrode 502. In this embodiment, each radial electrode, such as the first radial electrode 501, includes first branches 511 extending from a first side and second branches 512 extending from a second side. Each branch defines a first tip 521 on the first side, with a similar second tip 522 being defined on the second side. In an embodiment, distances between adjacent tips of adjacent branches are substantially similar, as further described with reference to FIG. 8.

FIG. 6

The embodiments described with reference to FIGS. 1 to 5 facilitate the implementation of a method of detecting irregularities in breast tissue by energizing a transmitter electrode, selected from a plurality of electrodes, to propagate an electric field through a detection region of breast tissue. Furthermore, a receiver electrode, selected from the remaining electrodes, is monitored to produce an output signal and the output signal is then analyzed to identify irregularities. Thus, the method depends upon the irregularities themselves experiencing a change in electrical permittivity, compared to normal tissue, to allow them to be detected. The transmitter electrode and the receiver electrode are located on a flexible substrate. The flexible substrate is substantially dome-shaped to define an internal surface arranged to accommodate breast tissue. Furthermore, the electrodes are evenly arranged over the domed-shaped flexible substrate by adopting an appropriate distribution that reflects the underlying geometry; an approach that cannot be achieved using a conventional Cartesian distribution.

The even arrangement of electrodes mounted on the dome-shaped flexible substrate results in the propagation of electric fields that follow a geometry sympathetic to the geometry of the underlying biology. In particular, irrespective of the actual position of the electrodes, it is desirable for electric fields of substantially similar strength to be generated, so that it is possible to make comparisons between different positions in space and similar positions over a period of time. Thus, by deploying electrodes in this geometry, it is possible to analyze the output signals to reliably detect irregularities.

As previously described, a preferred embodiment involves deploying a left dome-shaped apparatus over a left breast and a right dome-shaped apparatus over a corresponding right breast. Research suggests that it is very unusual for an irregularity to occur in both breasts at the same time at relatively similar locations. Consequently, an embodiment makes use of this observation by performing an analyzing step that includes comparing output signals derived from the left dome-shaped apparatus with similar output signals derived from the right dome-shaped apparatus. Thus, without having captured any historical data, it is possible for a comparison to be made in that, in a healthy state, similar signals should be derived from similar locations. If, however, a significant discrepancy is identified (the extent and polarity of which is not relevant) an alert signal may be generated. Furthermore, the process also identifies a particular location for further investigation; although this investigation must be carried out with respect to both the left side and the right side. Thus, this method allows an irregularity to be detected without reference to any historical data and without reference to an external database.

Figure 6:
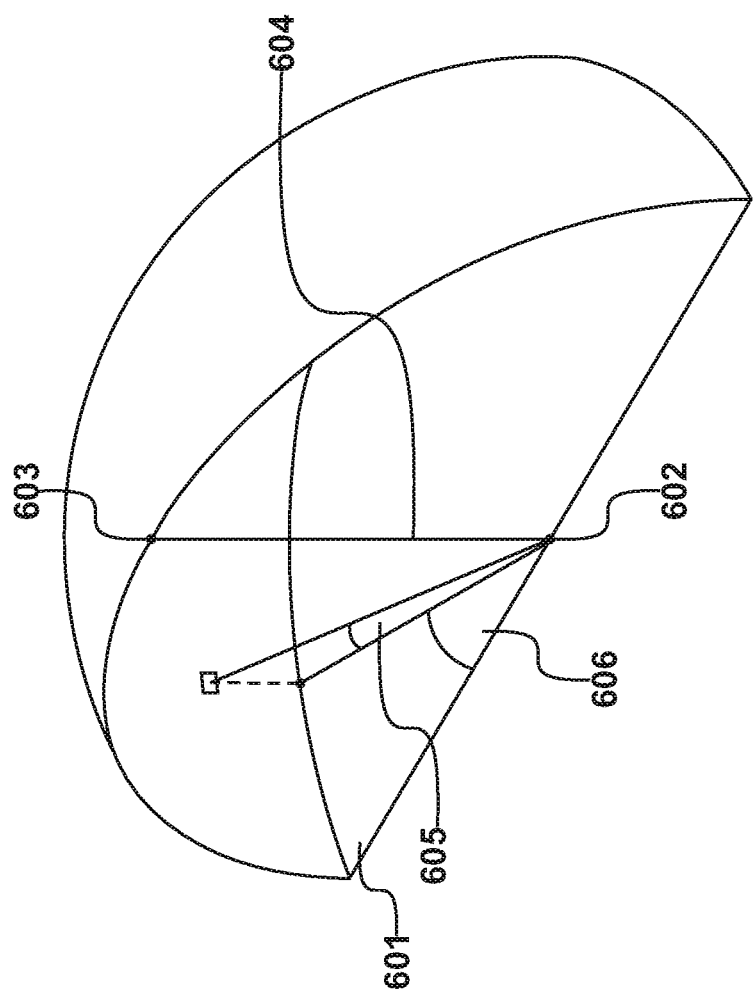
FIG. 6 illustrates a mathematical coordinate system.

To identify locations within the breast tissue, an embodiment models the region as a hemisphere, with locations specified by polar coordinates as illustrated in FIG. 6. In the geometric model of FIG. 6, an x-y plane 601 is defined, which at its centre has an origin 602. The origin 602 lies directly below a centre point 603 of the hemispherical dome.

Within the model, a radius 604 remains constant but within more sophisticated embodiments, it is possible for variations to occur; thereby allowing the model to adopt more natural irregular dome-shaped configurations.

In an embodiment, as described with reference to FIG. 4, substantially circular electrodes 411 to 415 are provided which, when centre point 603 is identified as a pole, may be considered substantially as lines of latitude. As such, the location of these circular electrodes may be identified by a latitude angle 605.

As described with reference to FIG. 5, an embodiment also includes radial electrodes 501, 502 etc., such that the position of any radial electrode may be defined by a longitude angle 606. Thus, any position within the region of the tissue may be defined by appropriate polar coordinates. These develop naturally from the adoption of the circular electrodes of FIG. 4 and the radial electrodes of FIG. 5, which in turn facilitate an appropriate adoption of an even electrode distribution over the dome-shaped substrate.

The radial electrodes also divide the hemisphere into a plurality of segments. Consequently, comparisons may be made between segments, such that an irregularity may be detected if a particular segment presents different output data from that of the other segments. Again, this provides a procedure that allows an irregularity to be detected without reference to historical data.

FIG. 7

Figure 7:
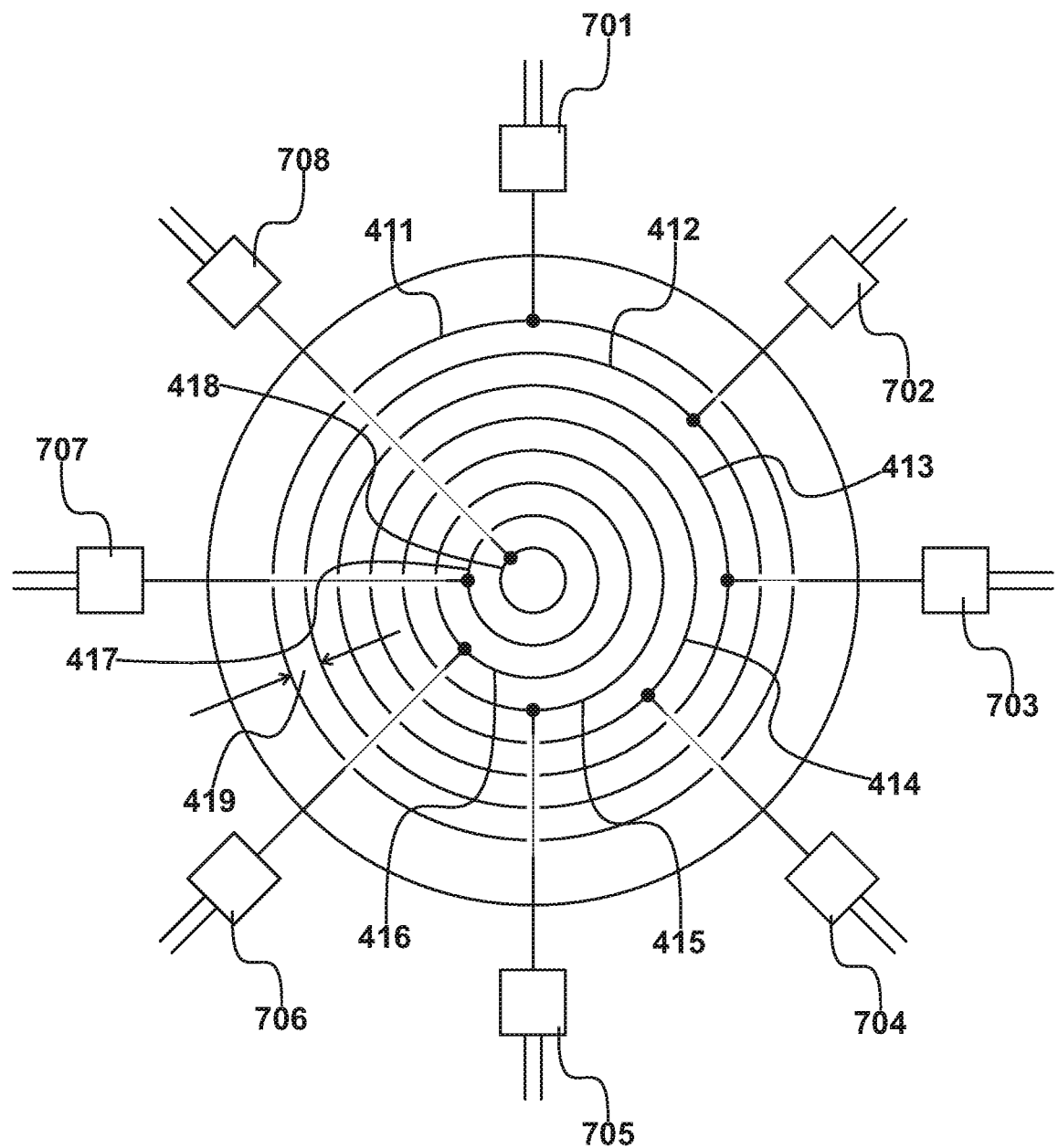
FIG. 7 shows a plan view of the internal surface of the dome-shaped substrate shown in FIG. 4.

A plan view of the inner surface 403 of the flexible substrate 301 is illustrated in FIG. 7. This shows the first circular electrode 411 to the fifth circular electrode 415, along with a sixth circular electrode 416, a seventh circular electrode 417 and an eight circular electrode 418. In an embodiment, a distance 419 between adjacent circular electrodes is substantially constant. Again, the intention is to provide similar output results at different locations of the region under investigation. In this embodiment, eight circular electrodes are present but other embodiments may have more or fewer electrodes, although a total number that is a power-of-two provides for efficient use of addressing capabilities.

The control circuit, within the support housing 302, provides a multiplexing environment in which various functionalities may be placed upon the electrodes present within the apparatus. An embodiment has a first set of electrodes on the inner surface 403 of the flexible substrate 301 and a second set of electrodes on the outer surface 404 of the flexible substrate 301. Separate multiplexing means are provided for each set of electrodes. Each respective multiplexing means is configured to select any electrode of its respective set to be a transmitter electrode while selecting any of the remaining electrodes in the set to be a receiver electrode. This allows sophisticated scanning techniques to be deployed, as detailed with reference to FIG. 13 and FIG. 14.

Thus, in this embodiment, a first multiplexing means 701 is attached to the first circular electrode 411, with a similar second multiplexing means 702 connected to the second circular electrode 412 and so on until an eighth multiplexing means 708 attached to the eighth circular electrode 418.

FIG. 8

Figure 8:
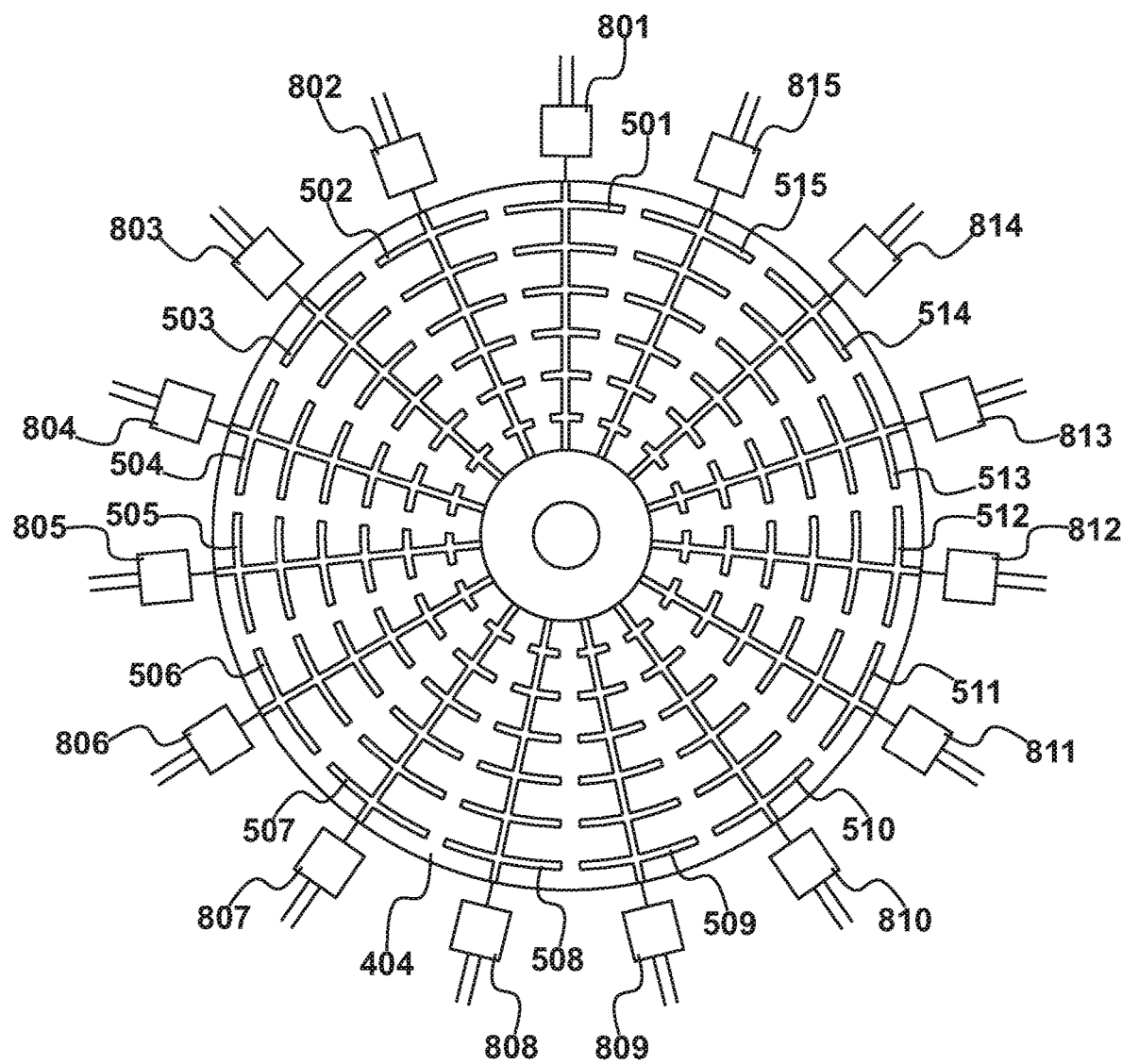
FIG. 8 shows a plan view of an outer surface of the substrate of FIG. 4.

A plan view of the outer surface 404 of the flexible substrate 301 is illustrated in FIG. 8, showing the radial electrodes, including the first radial electrode 501 and the second radial electrode 502, along with a third radial electrode 503 to a fifteenth radial electrode 515. Again, respective multiplexing means are provided for each radial electrode, consisting of a first radial multiplexing means 801 to a fifteenth radial multiplexing means 815. This allows any of the electrodes to be selected as a transmitter electrode, with any of the remaining electrodes being selected as a receiver electrode.

FIG. 9

Figure 9:
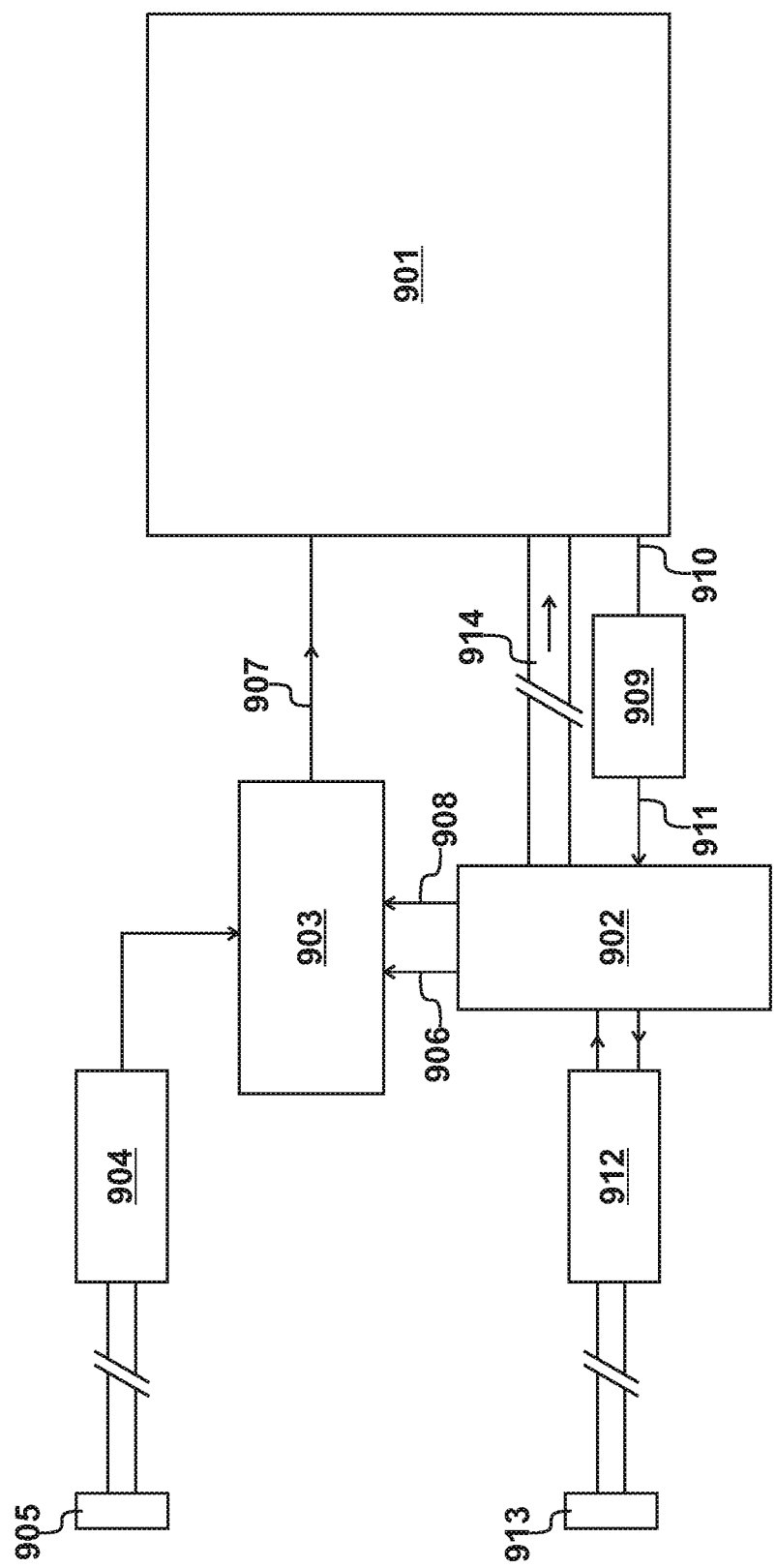
FIG. 9 shows a block diagram of the workings of the apparatus.

A block diagram of an apparatus embodying an aspect of the present invention is illustrated in FIG. 9. The flexible substrate, the first set of electrodes with first multiplexing means and the second set of electrodes with second multiplexing means are included within a multiplexing environment 901. The respective multiplexing means include de-multiplexers for selectively de-multiplexing energizing input pulses, along with multiplexers for multiplexing selected output signals.

A processor 902, implemented as a microcontroller in an embodiment, controls the multiplexing means to ensure that the same electrode cannot both be energized and monitored during the same coupling operation. An energizing circuit 903 is energized by a power supply 904, that in turn may receive power from an external source via a power input connector 905. In an embodiment, the power input connector 905 is connected to a rechargeable battery located within the support housing 302 or the support vest 207. A voltage-control line 906, from the processor 902 to the energizing circuit 903, allows the processor 902 to control the voltage (and hence the energy) of energizing signals supplied to the multiplexing environment 901 via a strobing line 907. The timing of each strobing signal is controlled by the processor 902 via a trigger-signal line 908.

An output from the multiplexing environment 901 is supplied to an analog processing circuit 909 over a first analog line 910. A conditioning operation is performed, by the analog processing circuit 909, allowing analog output signals to be supplied to the microcontroller via a second analog line 911. The processor 902 also communicates with a two-way data-communication circuit 912, thereby allowing a data interface 913 to connect wirelessly with an external mobile device.

In operation, the processor 902 supplies addresses over address busses 914 to the multiplexing environment 901, to achieve the required functionality. Thus, having supplied addresses to the multiplexing environment 901, an energizing voltage is supplied via the strobing line 907, resulting in an output signal being supplied to the processor 902 as part of a complete coupling operation. At the processor 902, a monitored analog signal is sampled to produce a digital representation that may be stored locally and/or uploaded via the data-output port. During each coupling operation, an electric field is established between an energized transmitter electrode and a monitored receiver electrode by capacitive coupling.

FIG. 10

Figure 10:
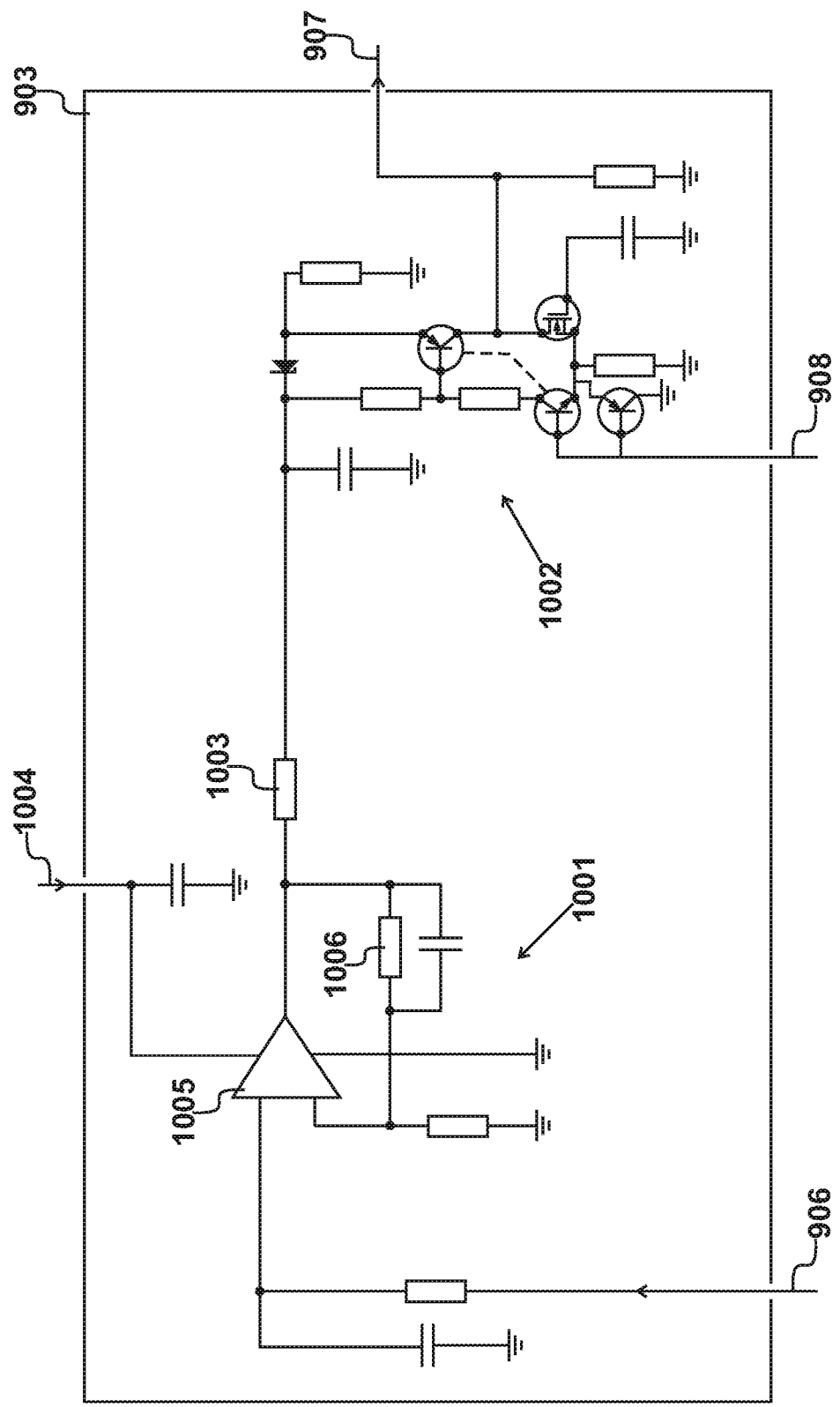
FIG. 10 shows a schematic representation of the energizing circuit identified in FIG. 9.

A schematic representation of the energizing circuit 903 is shown in FIG. 10. The energizing circuit 903 includes a voltage-control circuit 1001 connected to a strobing circuit 1002 via a current-limiting resistor 1003.

A voltage-input line 1004 receives energizing power from the power supply 904 to energize an operational amplifier 1005. The operational amplifier 1005 is configured as a comparator and receives a reference voltage via a feedback resistor 1006. This is compared against a voltage control signal received on the voltage-control line 906 to produce an input voltage for the strobing circuit 1002.

In the embodiment of FIG. 10, the strobing circuit 1002 includes two bipolar transistors configured as a Darlington pair, in combination with a field effect transistor. This creates strobing pulses with sharp rising edges and sharp falling edges, that are conveyed to the strobing line 907 after receiving a triggering signal on the trigger-signal line 908.

FIG. 11

Figure 11:
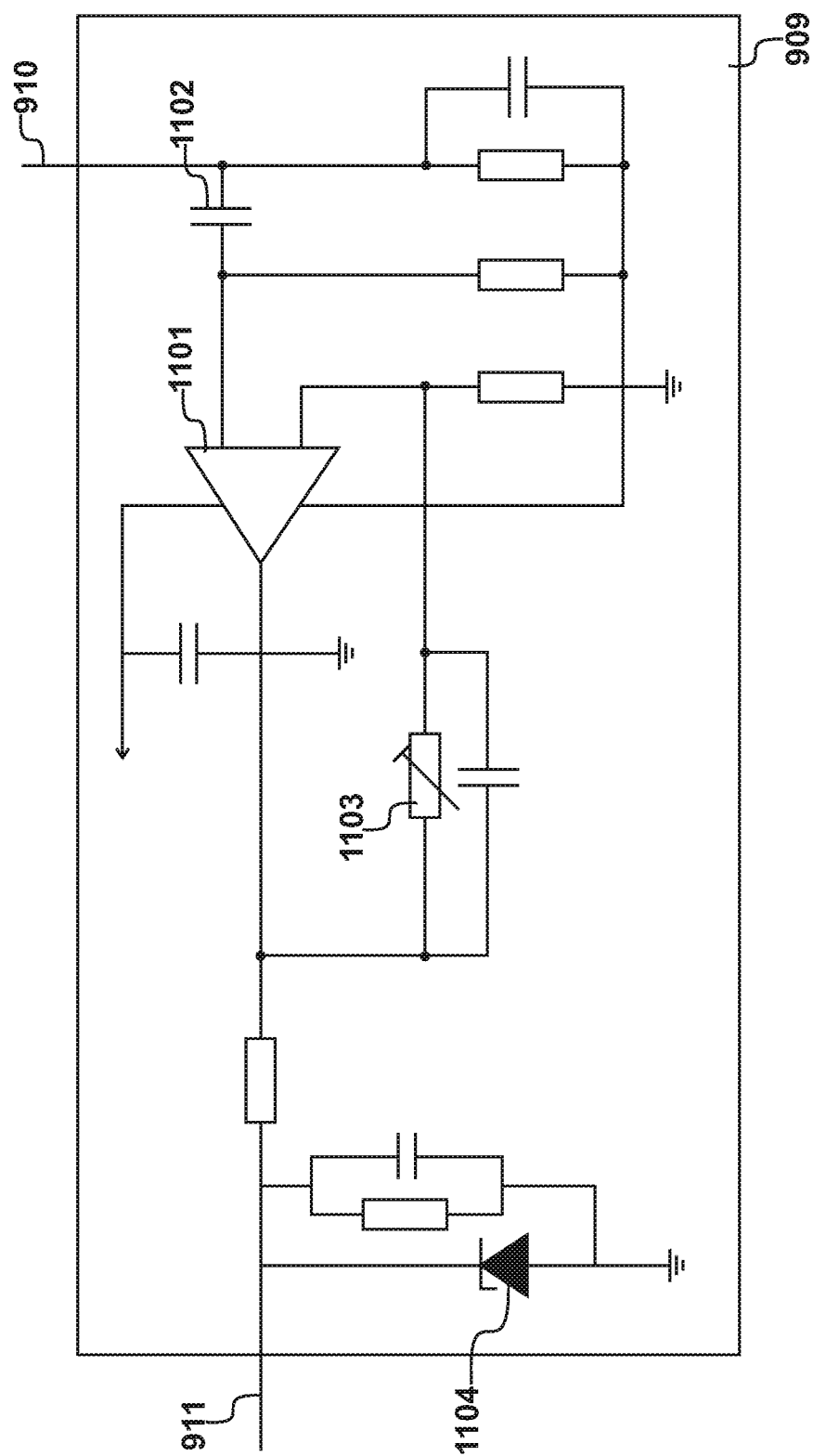
FIG. 11 shows an example of the analog processing circuit identified in FIG. 9.

An example of an analog processing circuit 909 is illustrated in FIG. 11. Signals received on the first analog line 910 are supplied to a buffering amplifier 1101 via a decoupling capacitor 1102. During an initial set-up procedure, a variable feedback resistor 1103 is trimmed to optimize the level of monitored signals supplied to the processor 902 via the second monitoring line 911. A Zener diode 1104 prevents excessive voltages being supplied to the processor 902.

FIG. 12

Figure 12:
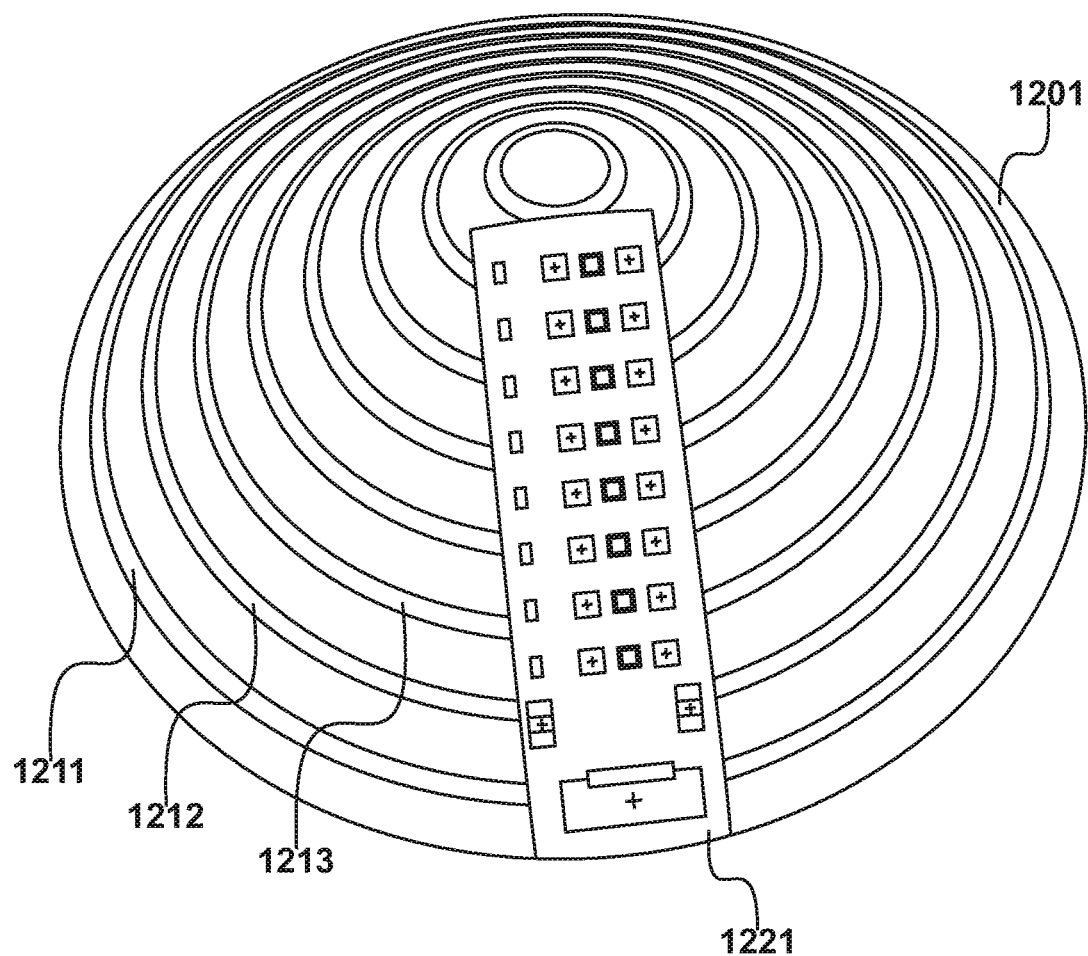
FIG. 12 shows an alternative arrangement of electrodes on an alternative flexible substrate.

An alternative embodiment is illustrated in FIG. 12, showing an alternative flexible substrate 1201. Again, the alternative flexible substrate 1201 is substantially dome-shaped to define an internal surface (obscured in FIG. 12) arranged to accommodate breast tissue. A plurality of electrodes, including a first alternative electrode 1211, a second alternative electrode 1212 and a third alternative electrode 1213 are evenly arranged over the dome-shaped flexible substrate 1201. The alternative electrodes achieve this even arrangement by being circular electrodes arranged as a plurality of concentric rings, in an arrangement similar to that described with reference to FIG. 4. However, in the alternative embodiment of FIG. 12, the concentric rings are on the external surface of the alternative flexible substrate 1201. Thus, in an embodiment, radial electrodes, substantially similar to those described with reference to FIG. 5, would be included on the internal surface of the alternative flexible substrate 1201.

The arrangement of the circular electrodes on the external surface of the alternative flexible substrate 1201 facilitates the provision of alternative multiplexing means 1221 directly upon the alternative flexible substrate 1201. In an embodiment, the alternative flexible substrate 1201 is initially constructed as a flat circular substrate from which a segment is then removed, such that the material can then be folded into the dome-shape illustrated in FIG. 12. Where the two radial ends of the removed segment join, connection is made to the alternative multiplexing means 1221.

FIG. 13

Figure 13:
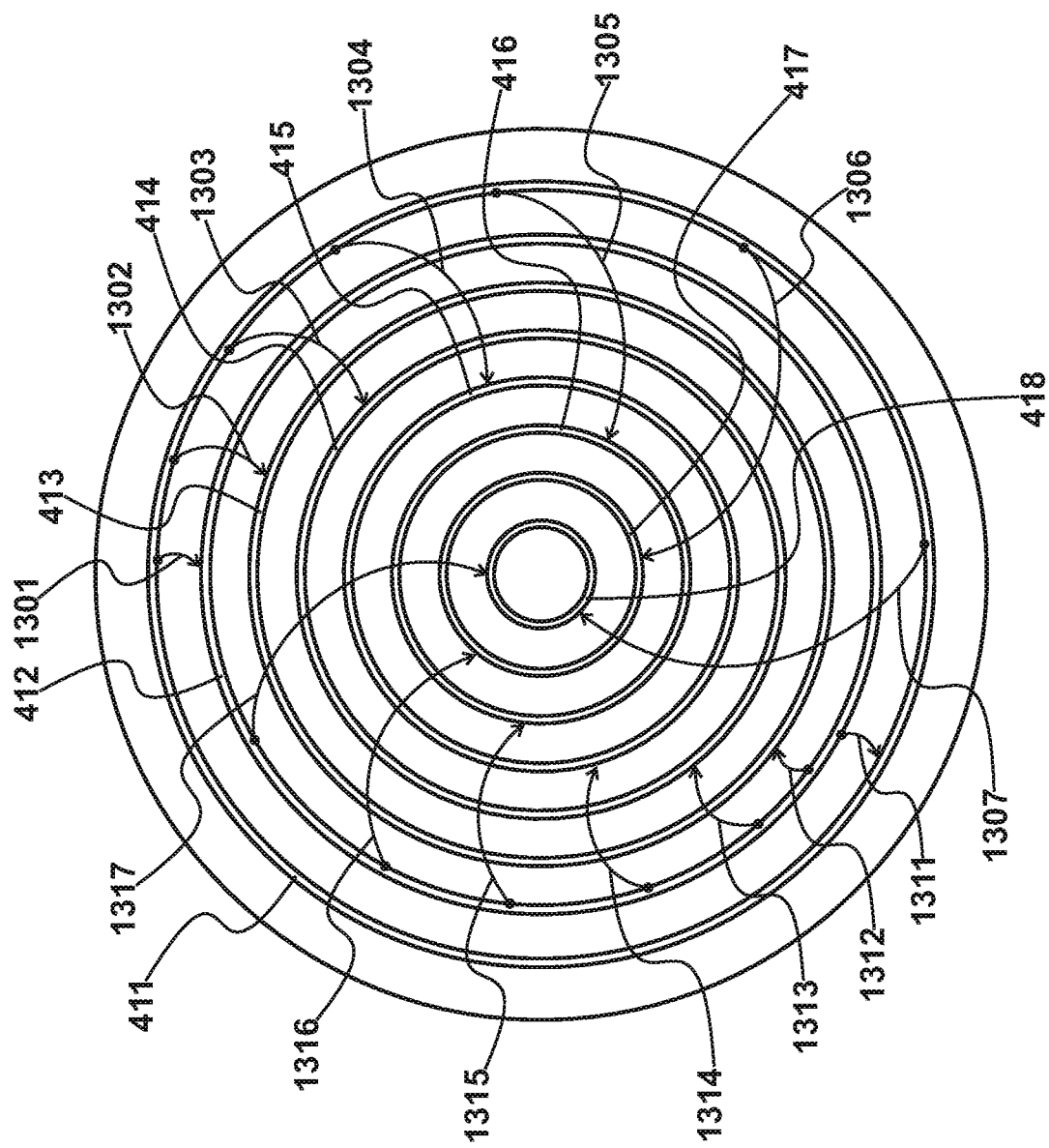
FIG. 13 illustrates the generation of electric fields between circular electrodes.

A plan view of the inner surface 403 of the flexible substrate 301 is illustrated in FIG. 13. Eight concentric circular electrodes 411 to 418 are mounted on the inner surface 403 of the flexible substrate 301. The multiplexing environment allows any of these electrodes to be selected as a transmitter with any of the remaining electrodes to be selected as a receiver. A similar approach is available with respect to the radial electrodes, as will be described with reference to FIG. 14.

In many known systems using electrodes of this type, scanning may be performed between adjacent electrodes and such an approach is adopted here. However, following a technique developed by the applicant and identified as "layering", it has been appreciated that when pairs of electrodes are selected that have a greater degree of separation, the resulting electric field penetrates deeper into the tissue for which an identification of irregularities is required.

In an embodiment, each of the circular electrodes is sequentially selected as a transmitter electrode. Furthermore, for each of the selected transmitter electrodes, each of the remaining circular electrodes is sequentially selected as a receiver electrode. Alternatively, it is possible to sequentially select each of the circular electrodes as a receiver electrode and, for each selected receiver electrode, sequentially select each of the remaining circular electrodes as a transmitter electrode. The multiplexing environment allows any electrode to be selected as a transmitter electrode or as a receiver electrode. The electrodes are not dedicated to a specific activity, thereby allowing the overall scanning procedure to make full use of the available electrode definition.

As previously described, an embodiment includes a first set of circular electrodes (on internal surface 403) and a second set of radial electrodes, on external surface 404, as further described with reference to FIG. 14. An overall cycle would involve completing a full sub-cycle with respect to the first set of electrodes followed by a second sub-cycle with respect to the second set of electrodes. This is then repeated until sufficient data has been collected.

A particular example of a layering technique is illustrated in FIG. 13. A sub-cycle starts by selecting the first electrode 411 as a transmitted electrode. During a first coupling operation, the second electrode 412 is selected as the receiver electrode and in an embodiment, a single sample is recorded following this coupling operation. However, as described with reference to FIG. 15 and FIG. 16, in an embodiment, multiple samples are recorded during each coupling operation. Thus, when the first electrode 411 is energized and the second electrode 412 is monitored, an electric field 1301 is generated between the first electrode 411 and the second electrode 412.

During the next coupling operation, the first electrode 411 is energized again but this time the third electrode 413 is monitored. A similar electric field 1302 is generated between the first electrode 411 and the third electrode 413 and this will penetrate deeper than electric field 1301 into the breast tissue. From the perspective of layering, the first electrode 411 is an electrode in common for plural coupling operations.

On the next coupling operation, the first electrode 411 is energized again but the fourth electrode 414 is monitored, resulting in deeper penetration as illustrated by a third electric field 1303. On the next coupling operation the first electrode 411 is energized again but the fifth electrode 415 is monitored, resulting in the generation of a fourth electric field 1304 going even further into the breast tissue. On the next coupling operation, the first electrode is energized again with the sixth electrode 416 being monitored, resulting in the generation of a fifth electric field 1305.

On the next coupling operation, the first electrode 411 is energized again with the seventh electrode 417 being monitored, resulting in the generation of a sixth electric field 1306. On the next coupling operation, the first electrode 411 is energized again with the eighth electrode 418 being monitored, resulting in the generation of a seventh electric field 1307. With wider and wider spacings between the coupled electrodes, deeper penetration into the breast tissue is achieved. Thus, after these coupling operations, with the first electrode 411 configured as an electrode-in-common transmitter, all of the remaining electrodes 412 to 418 will have been selected sequentially as the receiver electrode.

For the next coupling operation, the second electrode 412 is selected as the transmitter electrode with the first electrode 411 selected as the receiver, resulting in the generation of a second first-electric-field 1311. Thereafter, the second electrode 412 is again selected as the transmitter electrode (the electrode-in-common) and the third electrode 413 is selected as the receiver electrode, resulting in the generation of a second second-electric field 1312. These procedures continue, substantially as described above, sequentially resulting in the generation of a second third-electric field 1313, a second fourth-electric field 1314, a second fifth-electric field 1315, a second sixth-electric field 1316 and a second seventh-electric field 1317.

On the next coupling operation, the third electrode 413 is selected as the transmitter and again the remaining electrodes are sequentially selected as receiver electrodes. Similar procedures continue until the eighth electrode 418 is selected as the electrode-in-common transmitter, with all of the remaining electrodes then sequentially selected as the receiver electrode.

FIG. 14

Figure 14:
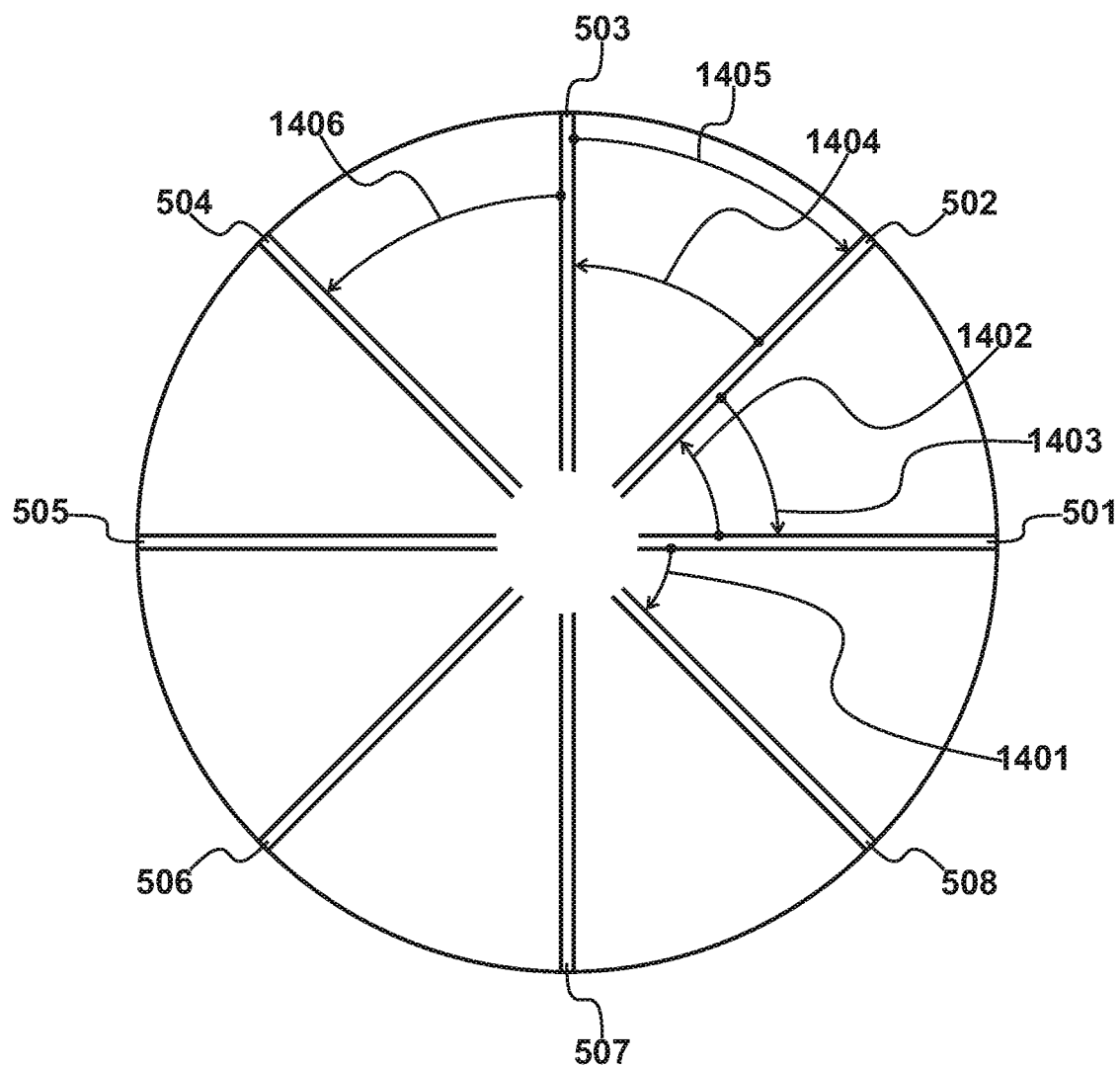
FIG. 14 shows the generation of electric fields between radial electrodes.

After a sub-cycle for the first set of electrodes has been completed, as described with reference to FIG. 13, a similar sub-cycle is performed with respect to the second set of electrodes, as illustrated in FIG. 14. In an embodiment, a first electrode is selected as a transmitter and the remaining electrodes are then sequentially selected as receivers. Alternatively, a first electrode could be selected as a receiver and the remaining electrodes sequentially selected as transmitters. In the embodiment of FIG. 14, an alternative approach is adopted in that a first electrode is selected as a transmitter, whereafter only adjacent radial electrodes are sequentially selected as receivers.

To initiate the sub-cycle, the first radial electrode 501 is selected as a transmitter. During a first coupling operation, the eighth radial electrode 508 is selected as a receiver, producing a first electric field 1401, followed by the second radial electrode 502 being selected as a receiver on the next coupling operation, producing a second electric field 1402. On the next coupling operation, the second radial electrode 502 is selected as the transmitter electrode and the first electrode 501 is selected as the receiver electrode, as illustrated by a third electric field 1403. On the next coupling operation, the second electrode 502 is again selected as the transmitter with the third radial electrode 503 selected as the receiver, as illustrated by a fourth electric field 1404.

On the next coupling operation, the third radial electrode 503 is selected as the transmitter electrode and the second radial electrode 502 is selected as the receiver electrode, as illustrated by a fifth electric field 1405. On the next coupling operation, the third electrode 503 continues to be selected as a transmitter and the fourth radial electrode 504 is selected as the receiver, as illustrated by a sixth electric field 1406. Thus, similar procedures are performed until all of the electrodes have been selected as a transmitter, with adjacent electrodes sequentially being selected as receivers.

More generally, two coupling operations are performed with an electrode-in-common and each electrode circumferentially adjacent to the electrode-in-common.

FIG. 15

An analog signal may be monitored at a receiver electrode because, during a coupling operation, it is capacitively coupled to a transmitter electrode. The resulting electric field passes through the tissue undergoing investigation and, from an electrical perspective, the tissue may be modelled as a capacitance 1501 in parallel with a resistance 1502. As is known in the art, the resistance 1502 will provide a conduction path for all signals and, in particular, the resistance 1502 will allow direct current (DC) signals to pass. The resistance 1502 may be identified as having a specific numerical resistance or the reciprocal of this value may be identified in terms of its conductance.

As is known in the art, the capacitance 1501 will allow transient signals to pass but will appear as an open circuit to non-transient values. Thus, non-alternating signals are blocked but alternating signals are allowed to pass. A measured impedance will therefore vary with the size of the capacitance 1501 and this in turn provides an indication of the electrical permittivity of the region of tissue being examined.

Figure 15:
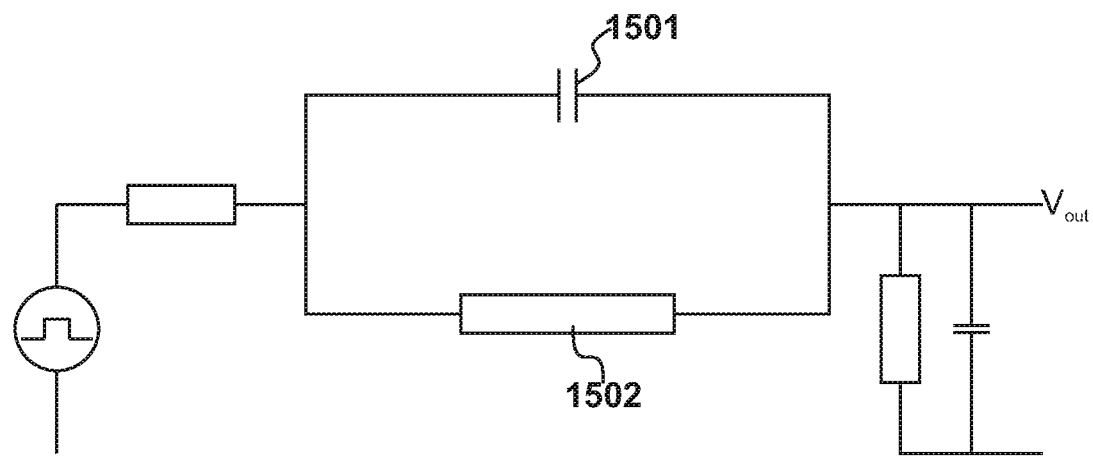
FIG. 15 shows an example of a monitored analog output signal.
Figure 15:
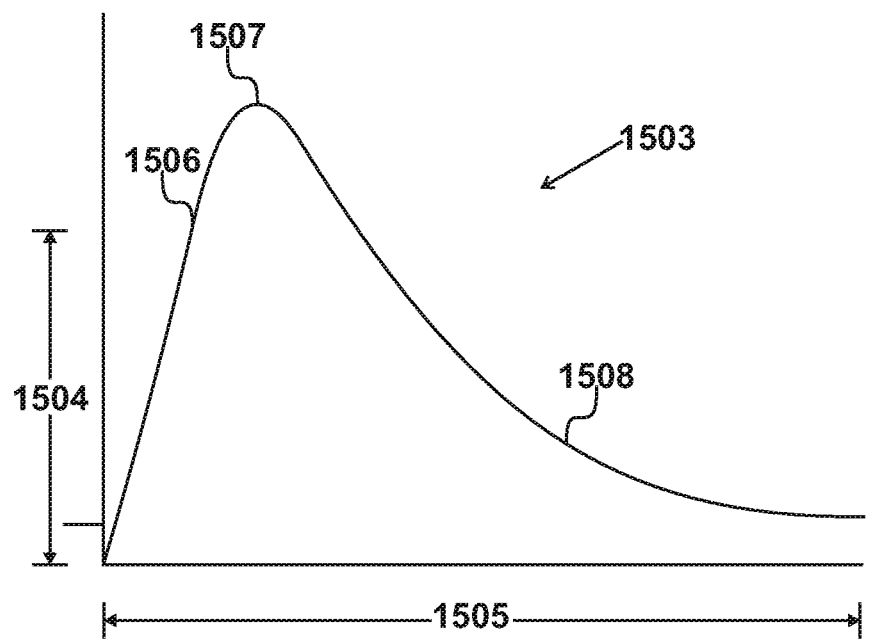

An example 1503 of a monitored analog output signal is shown in FIG. 15. In this example, output voltage 1504 has been plotted against time 1505. An output response may be identified as having a rising edge 1506, a peak 1507 and a falling edge 1508. In response to an input strobing signal, the rising edge 1506 may be seen as a charging portion and the falling edge 1508 may be seen as a discharging portion. Thus, each pulse 1503 may be seen as consisting of a very high frequency component at the beginning, followed by a DC level during the coupling operation.

It can therefore be appreciated that, in terms of transmission through the tissue, the capacitance 1501 provides a lower impedance during the rising portion 1506, leading to the peak value 1507. Thereafter, a DC level is maintained, therefore conductance through the discharge portion 1508 occurs at a rate that is determined predominantly by the resistance 1502.

Assessment of the peak value 1507 provides output data that is influenced predominantly by the permittivity of the tissue. Similarly, the rate at which the signal decays during portion 1508 provides data that is predominantly determined by the electrical conductively of the tissue.

FIG. 16

Figure 16:
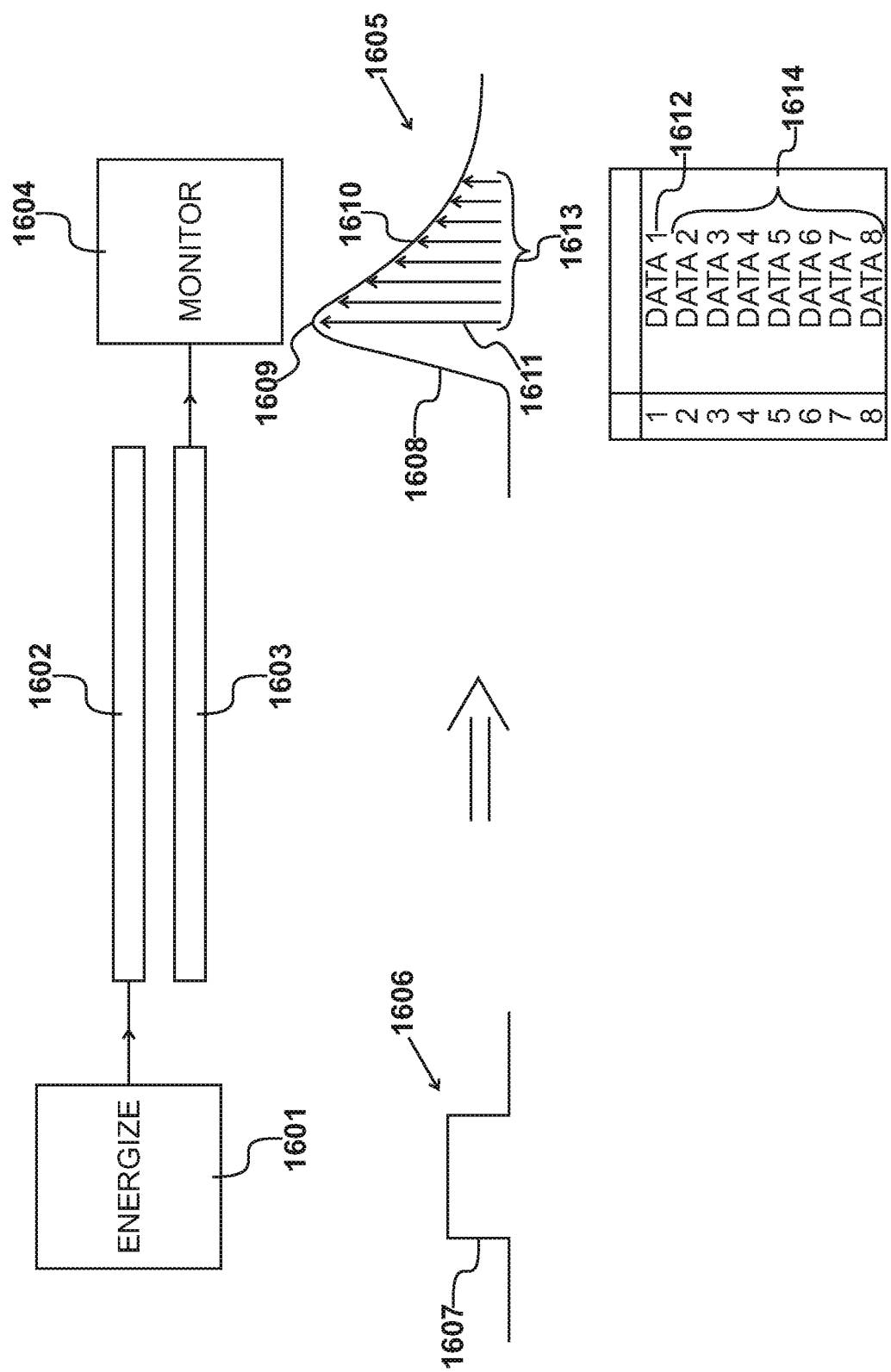
FIG. 16 illustrates multiple sampling of an analog output signal.

As illustrated in FIG. 16, an embodiment of the present invention includes a strobing circuit 1601 that energizes a transmitter electrode 1602 during a coupling operation. During each coupling operation, a receiver electrode 1603 is monitored, as illustrated at 1604, to produce an analog output signal 1605. During a coupling operation, an energizing pulse 1606 includes a sharp rising edge 1607. The receiver electrode 1603 is capacitively coupled to the transmitter electrode 1602 and, as such, the resulting analog output signal has characteristics determined by the impedance of the transmission environment. This results in the presentation of a rising slope 1608, a peak-value 1609 and a falling slope 1610.

The analog output signal is sampled, as illustrated by a first arrow 1611, to produce first sample data 1612. In addition, further sampling 1613 is performed to produce additional sample data 1614 during the strobing operation.

The first sampling step may be performed substantially at the peak value 1609 of the analog output signal. Furthermore, the further sampling step may produce additional sample data after the peak value. In the embodiment illustrated, the further sampling step produces seven instances (DATA 2-DATA 8) of additional sample data 1614.

In an enhanced embodiment, the multiplexing means are upgraded to allow multiple input samples to be received in parallel. The overall operation is performed first with respect to the first set of electrodes and then with respect to the second set of electrodes, as previously described. Similarly, electrodes are sequentially selected as transmitter electrodes. During a coupling operation, the selected transmitter electrode is energized, allowing input signals to be received. However, as an alternative to selecting individual receiver electrodes, all of the remaining electrodes within the set are monitored in parallel to produce multiple output signals. Furthermore, as previously described with respect to FIGS. 15 and 16, each of these output signals may be sampled a multiple number of times, thereby generating a rich data set in response to each coupling operation.

Under this enhanced mode of operation, for example, during a coupling operation, the first circular electrode 411 is energized. However, all of the remaining electrodes are monitored, such that electric fields 1301 to 1307 are generated simultaneously and output results from the receiver electrodes are sampled in parallel.

The invention claimed is:

1. An apparatus for examining breast tissue, comprising:
a first flexible dome-shaped substrate defining an internal surface arranged to accommodate breast tissue;
a set of substantially circular electrodes, each of said substantially circular electrodes forming one of a plurality of concentric rings, located on a first surface of said first flexible dome-shaped substrate; a set of substantially radial electrodes, each of said substantially radial electrodes forming a line, located on a second surface of said first flexible dome-shaped substrate;
an energizing circuit for energizing a transmitter electrode selected from said substantially circular electrodes or said substantially radial electrodes to propagate an electric field through a detection region of said breast tissue during a coupling operation; and
a monitoring circuit for receiving an output signal from a receiver electrode selected from remaining electrodes of said substantially circular electrodes and said substantially radial electrodes, wherein:
positions are identified within said detection region by coordinates established by said substantially circular electrodes and said substantially radial electrodes.

2. The apparatus of claim 1, further comprising multiplexing means configured to:
select any available electrode for energizing as said transmitter electrode; and
select a remaining electrode as said receiver electrode, wherein said transmitter electrode and said receiver electrode are capacitively coupled during said coupling operation.

3. The apparatus of claim 2, wherein:
said multiplexing means selects a first set of electrodes from said substantially circular electrodes and said substantially radial electrodes for selectively energizing and monitoring; and
said multiplexing means then selects an alternative second set of electrodes from said substantially circular electrodes and said substantially radial electrodes for selectively energizing and monitoring.

4. The apparatus of claim 1, wherein spacings between adjacent electrodes of said substantially circular electrodes are of a substantially similar size.

5. The apparatus of claim 1, wherein each of said substantially radial electrodes includes:
first branches extending from a first side; and
second branches extending from a second side.

6. The apparatus of claim 5, wherein:
each branch of said first branches defines a respective first tip;
each branch of said second branches defines a respective second tip; and
distances between adjacent tips of adjacent branches are substantially similar.

7. The apparatus of claim 1, further comprising:
a second substantially dome-shaped flexible substrate, wherein:
said first flexible dome-shaped substrate is supported within a wearable item; and
said second substantially dome-shaped flexible substrate is also supported within said wearable item.

8. The apparatus of claim 7, wherein said energizing circuit and said monitoring circuit are housed within a control unit; and
said control unit is located within said wearable item.

9. The apparatus of claim 8, wherein:
said control unit includes a rechargeable battery; and
said control unit is removable from said wearable item to facilitate the recharging of said rechargeable battery.

10. A method of examining breast tissue using electric fields created by electrodes, wherein:
a set of substantially circular electrodes, each of said substantially circular electrodes forming one of a plurality of concentric rings, located on a first surface of said first flexible dome-shaped substrate; a set of substantially radial electrodes, each of said substantially radial electrodes forming a line, located on a second surface of said first flexible dome-shaped substrate;
the method comprising the steps of:
energizing a selected transmitter electrode;
monitoring a selected receiver electrode, to propagate electric fields through a detection region of said breast tissue during respective coupling operations; and
identifying positions within said detection region by coordinates established by said substantially circular electrodes and said substantially radial electrodes.

11. The method of claim 10, further comprising the steps of:
deploying the first flexible dome-shaped substrate over a left breast; and deploying a second flexible dome-shaped substrate over a corresponding right breast, wherein the second flexible dome-shaped substrate comprises a set of electrodes; and comparing output signals derived from said first flexible dome-shaped substrate with output signals derived from similar positions on said second flexible dome-shaped substrate.

12. The method of claim 10, further comprising the steps of:
sequentially selecting each of said substantially circular electrodes as a transmitter electrode; and
for each selected transmitter electrode, sequentially selecting each of said remaining substantially circular electrodes as a receiver electrode.

13. The method of claim 10, further comprising the steps of:
sequentially selecting each of said substantially circular electrodes as a receiver electrode; and
for each selected receiver electrode, sequentially selecting each of said remaining substantially circular electrodes as a transmitter electrode.

14. The method of claim 10, further comprising the steps of:
sequentially selecting each of said substantially radial electrodes as a transmitter electrode; and
for each selected transmitter electrode, sequentially selecting adjacent substantially radial electrodes as a receiver electrode.

15. The method of claim 10, further comprising the steps of:
sequentially selecting each of said substantially radial electrodes as a receiver electrode; and
for each selected receiver electrode, sequentially selecting adjacent remaining substantially radial electrodes as a transmitter electrode.

16. The method of claim 10, further comprising the step of:

storing output data derived from permittivity values identified within a coordinate system; and comparing similarly located permittivity values recorded over a period of time.

17. The method of claim 10, further comprising the steps of:

sampling a monitored output signal during each coupling operation; and converting said sample to a digital representation thereof.

18. The method of claim 17, wherein each monitored output signal is first sampled substantially at a peak value for said monitored output signal.

19. The method of claim 18, further comprising the step of further sampling said monitored output signal a plurality of times after said peak value.

* * * * *